(12) United States Patent
Wagner et al.

(10) Patent No.: US 6,177,446 B1
(45) Date of Patent: Jan. 23, 2001

(54) FUNGICIDAL MIXTURE

(75) Inventors: Oliver Wagner, Bexbach; Karl Eicken, Wachenheim; Herbert Bayer; Hubert Sauter, both of Mannheim; Eberhard Ammermann, Heppenheim; Gisela Lorenz, Hambach, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/484,529

(22) Filed: Jan. 18, 2000

Related U.S. Application Data

(62) Division of application No. 08/849,126, filed as application No. PCT/EP95/04785 on Dec. 5, 1995, now Pat. No. 6,075,030.

(30) Foreign Application Priority Data

Dec. 16, 1994 (DE) .................................. 44 44 911

(51) Int. Cl.⁷ ............................ A01N 43/42; A01N 43/64
(52) U.S. Cl. .......................... 514/311; 514/312; 514/383
(58) Field of Search ..................... 514/312, 383, 514/311

(56) References Cited

U.S. PATENT DOCUMENTS 5,240,940 * 8/1993 Arnold et al. ...................... 514/312

FOREIGN PATENT DOCUMENTS

0196038 * 10/1986 (EP) .

* cited by examiner

*Primary Examiner*—Allen J. Robinson
(74) *Attorney, Agent, or Firm*—Keil & Weinkauf

(57) ABSTRACT

A composition comprising effective amounts of a) a compound of the formula I

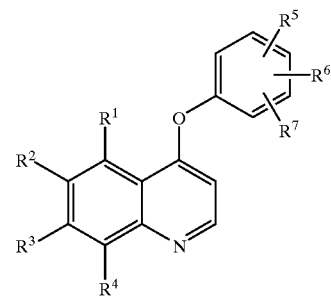

(I)

or an N-oxide or salt thereof, wherein $R^1$, $R^2$, $R^3$ and $R^4$ are hydrogen, hydroxyl, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$R^5$, $R^6$ and $R^7$ are hydrogen, hydroxyl, cyano, nitro, halogen, $C_1$–$C_7$-alkyl, $C_1$–$C_7$-haloalkyl, $C_1$–$C_7$-alkoxy, $C_1$–$C_7$-haloalkoxy, $C_1$–$C_7$-alkylthio, $C_1$–$C_7$-haloalkylthio, $C_1$–$C_7$-hydroxyalkyl, $C_2$–$C_4$-acyl, aryl or aryloxy, it being possible for the radicals with aryl to carry one to three of the following groups: cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, and d) (2RS,3SR)-1-[3-(2-chlorophenyl)-2-(4-fluorophenyl)oxiran-2-ylmethyl]-1H-1,2,4-triazole (IV)

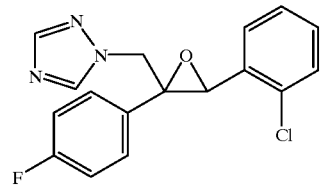

(IV)

exhibits a synergistic fungicidal activity.

20 Claims, No Drawings

FUNGICIDAL MIXTURE

This is a Divisional Application of application Ser. No. 08/849,126, filed on Jun. 16, 1997, (now U.S. Pat. No. 6,075,030) which is a National Stage Application under 35 U.S.C. 371, based on International Application No. PCT/EP 95/04,785, filed Dec. 05, 1995.

The present invention relates to a fungicidal mixture comprising
a) a compound of the formula I

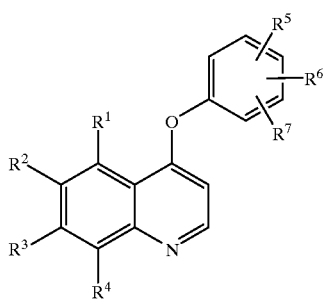

an N-oxide or a salt thereof, where the radicals are defined as follows:

$R^1, R^2, R^3$ and $R^4$ independently of one another are: hydrogen, hydroxyl, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio;

$R^5, R^6$ and $R^7$ independently of one another are: hydrogen, hydroxyl, cyano, nitro, halogen, $C_1$–$C_7$-alkyl, $C_1$–$C_7$-haloalkyl, $C_1$–$C_7$-alkoxy, $C_1$–$C_7$-haloalkoxy, $C_1$–$C_7$-alkylthio, $C_1$–$C_7$-haloalkylthio, $C_1$–$C_7$-hydroxyalkyl, $C_2$–$C_4$-acyl, aryl or aryloxy, it being possible for the radicals with aryl to have attached to them, in turn, one to three of the following groups: cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, or b) a compound of the formula II,

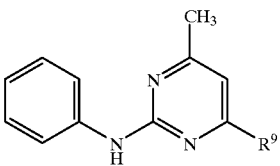

where the radicals are defined as follows:

$R^8$ is phenyl which can have attached to it one to three of the following groups: cyano, halogen, $C_1$–$C_4$-alkyl, $C_1$–$C_2$-haloalkyl and $C_1$–$C_4$-alkoxy, or pyrimidyl which can have attached to it a $C_1$–$C_3$-alkyl group and/or a phenoxy group, it being possible for the phenoxy group to have attached to it, in turn, one to three of the following substituents: cyano, halogen, $C_1$–$C_4$-alkyl, $C_1$–$C_2$-haloalkyl and $C_1$–$C_4$-alkoxy;

A is oxygen or oxymethylene (—OCH$_2$—);
X is CH or N;
Y is oxygen or NR, where R is hydrogen, $C_1$–$C_3$-alkyl or $C_1$–$C_3$-alkoxy, or c) a pyrimidine derivative of the formula III

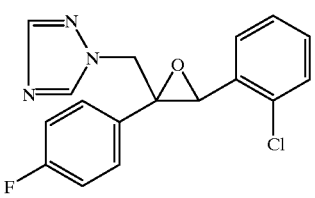

or a salt thereof: where the radical $R^9$ is methyl, propyn-1-yl or cyclopropyl, or d) (2RS,3SR)-1-[3-(2-chlorophenyl)-2-(4-fluorophenyl) oxiran-2-ylmethyl]-1H-1,2,4-triazole (IV)

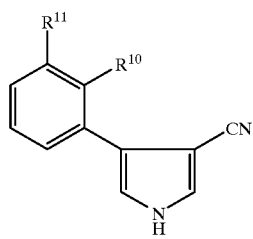

e) a compound of the formula V

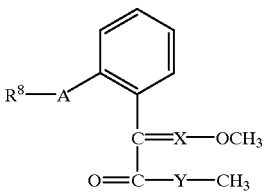

in which the radicals are as defined below:
$R^{10}$ is fluorine or chlorine;
$R^{11}$ is trifluoromethyl or chlorine, or
$R^{10}$ and $R^{11}$ together are a group —OCF$_2$O—,
in a synergistically active amount.

The invention furthermore relates to methods of controlling fungal pests using the compounds I and a compound II to V, or synergistic mixtures comprising them, and to the use of the compounds I, or the compounds II to V, for the preparation of such mixtures.

U.S. Pat. No. 5,240,940 and ACS Sympos. Ser. 443, page 538 to page 552 (1991) disclose compounds of the formula I, their fungicidal action and their preparation.

The literature (EP-A 253 213, EP-A 382 375, EP-A 398 692, EP-A 400 417) also discloses compounds of the formula II, their preparation and their action against fungal pests.

Also known are the pyrimidine derivatives III, their preparation and their action against fungal pests [$R^9$=methyl: DD-A 151 404 (common name: pyrimethanil); $R^9$=1-propynyl: EP-A 224 339 (common name: mepanipyrim); $R^9$=cyclopropyl: EP-A 310 550 (common name: cyprodinil)].

EP-A 196 038 discloses (2RS,3SR)-1-[3-(2-chlorophenyl)-2-(4-fluorophenyl)oxiran-2-ylmethyl]-1H-1, 2,4-triazole (IV) (INN name: epoxiconazole).

EP-A 318 704 ($R^{10}$=F, $R^{11}$=CF$_3$), EP-A 206 999 ($R^{10}$, $R^{11}$=—O—CF$_2$—O—: common name: fludioxonil) and EP-A 182 738 ($R^{10}$, $R^{11}$=chlorine: common name: fenpiclonil) also disclose the compounds of the general formula V.

With a view to reducing the rates of application and to improving the spectrum of action of the known compounds, it is an object of the present invention to provide mixtures which have an improved activity against fungal pests while the total amount of active ingredients applied is reduced (synergistic mixtures).

We have found that this object is achieved by the mixtures defined at the outset. Moreover, it has been found that fungal pests can be controlled more efficiently when the compounds I and the compounds II to V are applied simultaneously, i.e. jointly or separately, or when the compounds I and the compounds II to V are applied in succession, than when the compounds I or II to V are used alone.

Relative to the C=X double bond, the compounds of the formula II can exist in the E or the Z configuration (relative to the $OCH_3$ and $CO-YCH_3$ group). Accordingly, they can be used in the mixture according to the invention either in the form of the pure isomers or in the form of a mixture of E/Z isomers. The mixture of E/Z isomers or the E isomer is preferably used, the E isomer being particularly preferred in many cases.

Due to the basic character of the ring nitrogen atom or the NH group, the compounds I and III are capable of forming salts with inorganic or organic acids or with metal ions.

Examples of inorganic acids are hydrohalic acids, such as hydrogen fluoride, hydrogen chloride, hydrogen bromide and hydrogen iodide, sulfuric acid, phosphoric acid and nitric acid.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having 1 to 20 carbon atoms), arylsulfonic acids or aryldisulfonic acids (aromatic radicals such as phenyl and naphthyl which have attached to them one or two sulfonic acid groups), alkylphosphonic acids (phosphonic acids having straight-chain or branched alkyl radicals having 1 to 20 carbon atoms), arylphosphonic acids or aryldiphosphonic acids (aromatic radicals such as phenyl and naphthyl which have attached to them one or two phosphoric acid radicals), it being possible for the alkyl or aryl radicals to have attached to them further substituents, for example p-toluenesulfonic acid, salicylic acid, p-aminosalicylic acid, 2-phenoxybenzoic acid, 2-acetoxybenzoic acid and the like.

Suitable metal ions are, in particular, the ions of the elements of the second Main Group, in particular calcium and magnesium, of the third and fourth Main Group, in particular aluminum, tin and lead, and of the first to eighth Sub-group, in particular chromium, manganese, iron, cobalt, nickel, copper and zinc. Particularly preferred metal ions are those of the elements of the Sub-groups of the fourth period. The metal can exist at the various valency levels which they assume.

Furthermore, the compounds I can be converted in a manner known per se to give the N-oxides (cf. U.S. Pat. No. 5,240,940).

Compounds I and their salts or N-oxides which are preferably used for providing the fungicidal mixtures according to the invention are those where the radicals are defined as follows:

$R^1,R^2,R^3$ and $R^4$ independently of one another are hydrogen, halogen, $C_1$–$C_2$-alkyl, $C_1$–$C_2$-haloalkyl, $C_1$–$C_2$-alkoxy, $C_1$–$C_2$-haloalkoxy or $C_1$–$C_2$-alkylthio; and $R^5,R^6$ and $R^7$ independently of one another are hydrogen, nitro, cyano, halogen, $C_1$–$C_4$-alkyl, $C_1$–$C_4$-haloalkyl, $C_1$–$C_4$-alkoxy or phenyl.

With a view to the applicability as components in the mixture, particularly preferred compounds are the compounds Ia as shown in Table 1 below.

TABLE 1

(Ia)

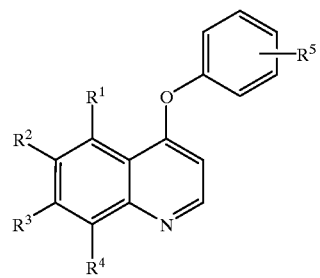

| No. | $R^1$ | $R^2$ | $R^3$ | $R^4$ | $R^5$ |
|---|---|---|---|---|---|
| 1 | H | H | Cl | H | 2-F |
| 2 | H | H | Cl | H | 2-C(CH$_3$)$_3$ |
| 3 | H | H | Cl | H | 2-CH$_3$ |
| 4 | H | H | Cl | H | 2-OCH$_3$ |
| 5 | H | H | Cl | H | 3-F |
| 6 | H | H | Cl | H | 3-Cl |
| 7 | H | H | Cl | H | 3-CF$_3$ |
| 8 | H | H | Cl | H | 3-CN |
| 9 | H | H | Cl | H | 3-OCH$_3$ |
| 10 | H | H | Cl | H | 3-phenyl |
| 11 | H | H | Cl | H | 4-Cl |
| 12 | H | H | Cl | H | 4-Br |
| 13 | H | H | Cl | H | 4-CF$_3$ |
| 14 | H | H | Cl | H | 4-CH$_3$ |
| 15 | H | H | Cl | H | 4-CH(CH$_3$)$_2$ |
| 16 | H | H | Cl | H | 4-CN |
| 17 | H | H | Cl | H | 2-Cl—4-F |
| 18 | H | H | Cl | H | 2,4-di-Br |
| 19 | H | H | Cl | H | 2,4-di-NO$_2$ |
| 20 | H | H | Cl | H | 2-CH$_3$—4-F |
| 21 | H | H | Cl | H | 2,6-di-F |
| 22 | H | H | Cl | H | 2,4,6-tri-CH$_3$ |
| 23 | F | H | H | H | 4-F |
| 24 | Cl | H | H | H | 4-F |
| 25 | NO$_2$ | H | H | H | 4-F |
| 26 | H | F | H | H | 4-F |
| 27 | H | Cl | H | H | 4-F |
| 28 | H | CH$_3$ | H | H | 4-F |
| 29 | H | NO$_2$ | H | H | 4-F |
| 30 | H | OC$_2$H$_5$ | H | H | 4-F |
| 31 | H | H | F | H | 4-F |
| 32 | H | H | Cl | H | 4-F |
| 33 | H | H | Br | H | 4-F |
| 34 | H | H | NO$_2$ | H | 4-F |
| 35 | H | H | OCF$_3$ | H | 4-F |
| 36 | H | H | C$_2$H$_5$ | H | 4-F |
| 37 | H | H | SCF$_3$ | H | 4-F |
| 38 | H | H | O—C$_2$H$_5$ | H | 4-F |
| 39 | H | H | H | F | 4-F |
| 40 | H | H | H | Cl | 4-F |
| 41 | H | H | H | CF$_3$ | 4-F |
| 42 | F | H | F | H | 4-F |
| 43 | O—CH$_3$ | H | O—CH$_3$ | H | 4-F |
| 44 | Cl | F | H | H | 4-F |
| 45 | Cl | Cl | H | H | 4-F |
| 46 | Cl | CH$_3$ | H | H | 4-F |

TABLE 1-continued (Ia)

[Structure: quinoline with substituents R¹, R², R³, R⁴ on ring carbons and O-phenyl-R⁵ group at position 4]

| No. | R¹ | R² | R³ | R⁴ | R⁵ |
|---|---|---|---|---|---|
| 47 | H | Br | H | Cl | 4-F |
| 48 | H | Cl | H | OH | 4-F |
| 49 | H | O—CH₃ | H | NO₂ | 4-F |
| 50 | H | F | Cl | H | 4-F |
| 51 | H | CH₃ | Cl | H | 4-F |
| 52 | H | H | Cl | Cl | 4-F |
| 53 | Cl | H | H | Cl | 4-F |
| 54 | Cl | F | Cl | H | 4-F |
| 55 | H | H | Cl | CN | 4-F |
| 56 | Cl | CH₃ | Cl | H | 4-F |
| 57 | Cl | Cl | Cl | H | 4-F |
| 58 | Cl | Cl | Cl | Cl | 4-F |
| 59 | H | H | H | Cl | 2-F—4-Br |
| 60 | H | H | H | Cl | 2,3-di-CH₃ |
| 61 | H | H | H | Cl | 2-F—4-Cl |
| 62 | H | H | H | Cl | 2,4-di-Cl—6-F |
| 63 | H | H | H | Cl | 2,4-di-F |
| 64 | H | H | H | Cl | 2,4-di-CH₃ |
| 65 | H | H | H | Cl | 2-C₂H₅ |
| 66 | H | H | H | Cl | 2-CH₃—4-F |
| 67 | H | H | H | Cl | 3-CH₃—4-Cl |
| 68 | H | H | Cl | H | H |
| 69 | Cl | H | Cl | H | H |
| 70 | H | H | Cl | H | 4-C(CH₃)₃ |

Very particularly preferred compounds are the compounds Ia as shown in Table 2, and the hydrochloride and N-oxide of compound 8 mentioned therein.

TABLE 2

| No. | R¹ | R² | R³ | R⁴ | R⁵ |
|---|---|---|---|---|---|
| 1 | H | H | Cl | H | 2-Cl |
| 2 | H | H | Cl | H | 2-Br |
| 3 | H | H | Cl | H | 2-CN |
| 4 | H | H | Cl | H | 2-CF₃ |
| 5 | H | H | Cl | H | 2-NO₂ |
| 6 | H | H | Cl | H | 4-F |
| 7 | H | H | Cl | H | 2,4-di-F |
| 8 | Cl | H | Cl | H | 4-F |
| 9 | H | H | H | Cl | 2-Cl-4-F |
| 10 | CH₃ | H | CH₃ | H | 4-F |

U.S. Pat. No. 5,240,940 and/or ACS Sympos. Ser. 443, page 538 to page 552 (1991) disclose the compounds of the formula Ia mentioned in or in connection with Tables 1 and 2.

Preferred compounds II for providing the fungicidal mixtures according to the invention

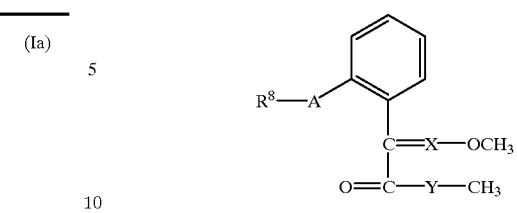

(II)

are those where the radicals are defined as follows:

R⁸ is phenyl which can have attached to it one to three of the following groups: cyano, halogen, $C_1$–$C_2$-alkyl, $C_1$–$C_2$-haloalkyl and $C_1$–$C_2$-alkoxy, or pyrimidyl which can have attached to it a $C_1$–$C_2$-alkyl group and/or a phenoxy group, it being possible for the phenoxy group, in turn, to have attached to it one to three of the following substituents: cyano, halogen, $C_1$–$C_2$-alkyl, $c_1$–$C_2$-haloalkyl and $C_1$–$C_2$-alkoxy, A is oxygen or oxymethylene (—OCH₂—);

X is CH or N; and

Y is oxygen or NR, where R is hydrogen, $C_1$–$C_2$-alkyl and $C_1$–$C_2$-alkoxy.

Particularly preferred fungicidal mixtures are those which comprise compounds II where the radicals are defined as follows:

R⁸ is phenyl which can have attached to it one to three of the following groups: halogen, methyl, trifluoromethyl and methoxy, A is oxymethylene (—OCH₂—), X is CH or N; and Y is oxygen or NR, where R is hydrogen, methyl and methoxy.

Other particularly preferred fungicidal mixtures are those which comprise compounds II where the radicals are defined as follows:

R⁸ is pyrimidyl, in particular pyrimidin-4,6-diyl which can have attached to it a methyl group and/or a phenoxy group, it being possible for the phenoxy group, in turn, to have attached to it one to three of the following substituents: cyano, halogen, methyl, trifluoromethyl and methoxy, A is oxygen;

X is CH or N; and

Y is oxygen or NR, where R is hydrogen, methyl or methoxy.

Other particularly preferred mixtures are those which comprise a compound of the formula II where R⁸ is 2-methylphenyl or 2,5-dimethylphenyl, A is oxymethylene, X is N and Y is oxygen or NH.

In addition, mixtures are preferred which comprise a compound of the formula II where R⁸ is 2-methylphenyl or 2,5-dimethylphenyl, A is oxymethylene, X is N and Y is NH.

Other preferred mixtures are those which comprise a compound of the formula II where R⁸ is 6-(2-cyanophenoxy)pyrimidin-4-yl, A is oxygen, X is CH and Y is oxygen.

With a view to the applicability as components in the mixture, particularly preferred compounds are the compounds II.A, II.B, II.C, II.D and II.E.

(II.A)
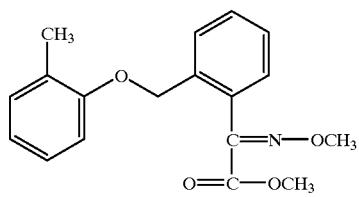

(II.B)
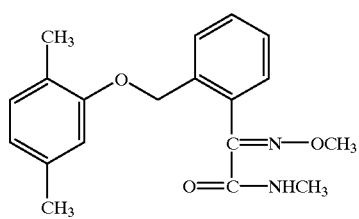

(II.C)
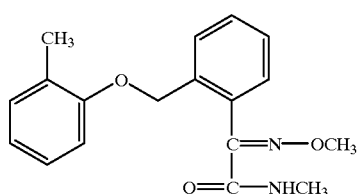

(II.D)
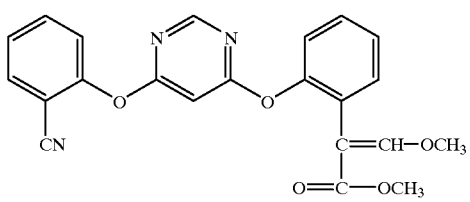

(II.E)
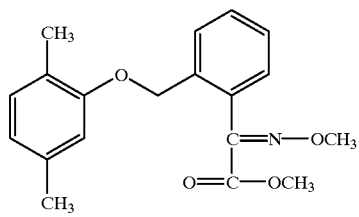

Compounds V.A, V.B and V.C below are preferably used for providing the fungicidal mixtures according to the invention:

(V.A)
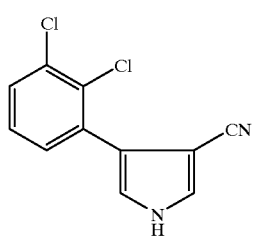

(V.B)
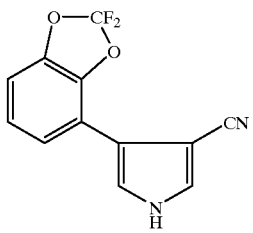

(V.C)
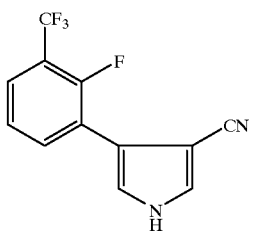

Preferably, the pure active ingredients I and II to V are employed for providing the mixtures, to which further active ingredients against fungal pests or other pests such as insects, arachnids or nematodes, or else herbicidal or growth-regulating active ingredients or fertilizers may be admixed, as required.

The mixtures of the compounds I and II to V, of the compounds I and II to V, are applied simultaneously, i.e. jointly or separately or in succession, and are distinguished by an outstanding activity against a broad spectrum of phytopathogenic fungi, in particular from the classes of the Ascomycetes, Deuteromycetes, Phycomycetes and Basidiomycetes. Some of them act systemically and can therefore also be used as leaf- and soil-acting fungicides.

They are particularly important for controlling a large number of fungi on a variety of crop plants such as cotton, vegetable species (for example cucumbers, beans and cucurbits), barley, grass, oats, coffee, maize, fruit plants, rice, rye, soya bean, grapevine, wheat, ornamentals, sugar cane and a variety of seeds.

They are especially suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Puccinia* species in cereals, *Rhizoctonia* species in cotton and turf, *Ustilago* species in cereals and sugar cane, *Venturia inaequalis* (scab) in apples, *Helminthosporium* species in cereals, *Septoria nodorum* in wheat, *Botrytis cinera* (gray mold) in strawberries and grapevines, *Cercospora arachidicola* in groundnuts, *Pseudocercosporella herpotrichoides* in wheat and barley, *Pyricularia oryzae* in rice, Phytophthora infestansin potatoes and tomatoes, *Plasmopara viticola* in grapevines, *Alternaria* species in vegetables and fruit, and *Fusarium* and *Verticillium* species.

They can furthermore be used in the protection of materials (for example the protection of wood), for example against *Paecilomyces variotii*.

The compounds I and II to V can be applied simultaneously, ie. jointly or separately, or in succession. If they are applied separately, the sequence has generally no effect on the result.

The compounds I and II to V are usually applied in a ratio by weight of 10:1 to 0.1:1, preferably 5:1 to 0.2:1, especially 3:1 to 0.3:1.

Depending on the nature of the desired effect, the rates of application of the mixtures according to the invention are 0.01 to 3 kg/ha, preferably 0.1 to 1.5 kg/ha, especially 0.4 to 1.0 kg/ha. The rates of application are 0.01 to 0.5 kg/ha in the case of the compounds I, preferably 0.05 to 0.5' kg/ha, especially 0.05 to 0.2 kg/ha. The rates of application for the compounds II to V are, accordingly, 0.1 to 1.0 kg/ha, preferably 0.4 to 1.0 kg/ha, especially 0.4 to 0.8 kg/ha.

In the treatment of seed, rates of application of 0.001 to 50 g of the mixture per kg of seed are generally used, preferably 0.01 to 10 g/kg, especially 0.01 to 8 g/kg.

If, in the case of plants, pathogenic fungal pests are to be controlled, the compounds I and II to V or the mixtures of the compounds I and II to V are applied separately or jointly by spraying or dusting the seeds, the plants or the soils before or after sowing the plants, or before or after plant emergence.

The fungicidal synergistic mixtures according to the invention, or the compounds I and II to V, can be processed for example in the form of ready-to-spray solutions, powders and suspensions or in the form of high-percentage aqueous, oily or other suspensions, dispersions, emulsions, oil dispersions, pastes, dusts, spreading materials or granules, and applied by means of spraying, atomizing, dusting, spreading or pouring. The use form depends on the intended use; in any case, it should guarantee as fine and uniform a distribution of the mixture according to the invention as possible.

The formulations are prepared in a manner known per se, for example by adding solvents and/or carriers. Inert additives such as emulsifiers or dispersants are customarily admixed to the formulations.

Suitable surfactants are the alkali metal, alkaline earth metal or ammonium salts of aromatic sulfonic acids, for example lignosulfonic acid, phenolsulfonic acid, naphthalenesulfonic acid and dibutylnaphthalenesulfonic acid, and of fatty acids, alkyl- and alkylaryl sulfonates, alkyl, lauryl ether and fatty alcohol sulfates, and salts of sulfated hexa-, hepta- and octadecanols or of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ether, ethoxylated isooctyl-, octyl- or nonylphenol, alkylphenol polyglycol ethers or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, spreading materials and dusts can be prepared by mixing or concomitantly grinding the compounds I to V or the mixture of the compounds I and II to V together with a solid carrier.

Granules (e.g. coated granules, impregnated granules and homogeneous granules) are conventionally prepared by binding the active ingredient, or active ingredients, to a solid carrier.

Fillers or solid carriers are, for example, mineral earths such as silica gel, silicic acids, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas and products of vegetable origin, such as cereal meal, tree bark meal, wood meal and nutshell meal, cellulose powder or other solid carriers.

The formulations generally comprise 0.1 to 95% by weight, preferably 0.5 to 90% by weight, of one of the compounds I to V or of the mixture of the compounds I and II to V. The active ingredients are employed in a purity of 90% to 100%, preferably 95% to 100% (in accordance with NMR spectrum or HPLC).

The compounds I to V or the mixtures or the relevant formulations are used by treating the fungal pests or the plants, seeds, soils, areas, materials or rooms to be protected against them with a fungicidally active amount of the mixture or, in the case of separate application, of the compounds I and II to V. Application may be effected before or after infection with the fungal pests.

Use example: Action against powdery mildew of wheat (curative)

Leaves of wheat seedlings cv. "Fruhgold" in pots were inoculated with spores of powdery mildew of wheat (*Erysiphe graminis* f. sp. *tritici*) and, 24 hours later, sprayed to runoff point with aqueous preparations of active ingredient which comprised 80% by weight of active ingredient and 20% by weight of emulsifier in the dry matter. After the aqueous preparations of active ingredient had dried on, the test plants were subsequently placed in a greenhouse at from 20 to 22° C. and a relative atmospheric humidity of 75 to 80%. After 7 days, the extent of mildew development was determined.

The visual scores of the percentage of diseased leaf area were converted into degrees of efficacy as a percentage of the untreated control. A degree of efficacy of 0 means the same disease level as in the case of the untreated control, a degree of efficacy of 100 is a disease level of 0%. The degrees of efficacy to be expected for combinations of active ingredients were determined by Colby's formula (S. R. Colby "Calculating synergistic and antagonistic responses of herbicide combinations", Weeds 15, pages 20 to 22 (1967)) and compared with the observed degrees of efficacy.

The tests were carried out using the following 4 compounds, which were assigned the symbols (A), (B), (C) and (D) for reasons of simplicity:

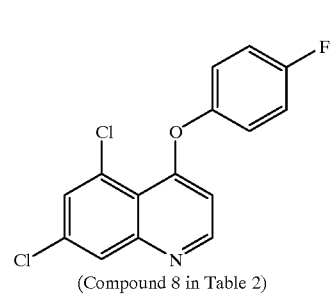

(A)

(Compound 8 in Table 2)

-continued

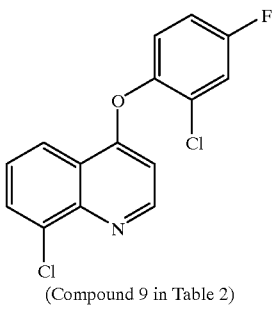

(Compound 9 in Table 2)

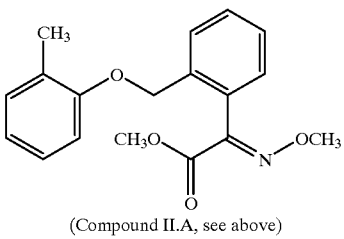

(Compound II.A, see above)

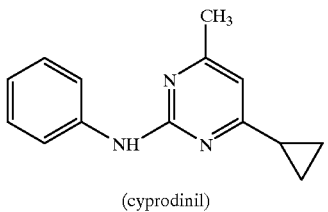

(cyprodinil)

A) Untreated control: disease level 44%

TABLE A.1

Degree of efficacy of the individual active ingredients

| Active ingredient | Concentration of active ingredient in the spray mixture [ppm] | Degree of efficacy [% of the untreated control] |
|---|---|---|
| (A) | 16 | 53 |
|  | 4 | 5 |
| (B) | 16 | 5 |
| (C) | 1 | 64 |
|  | 0.25 | 0 |

TABLE A.2

Degree of efficacy of the mixture

| Mixture of active ingredients | Observed degree of efficacy | Expected degree of efficacy |
|---|---|---|
| 16 ppm (A) + 1 ppm (C); Mixing ratio 16:1 | 100 | 83 |
| 4 ppm (A) + 0.25 ppm (C); Mixing ratio 16:1 | 53 | 5 |
| 16 ppm (B) + 1 ppm (C); Mixing ratio 16:1 | 98 | 66 |

Test result: The observed degree of efficacy in all mixing ratios is higher than calculated in advance using Colby's formula.

B) Untreated control: disease level 99%

The test was carried out as described for A).

TABLE B.1

Degree of efficacy of the individual active ingredients

| Active ingredient | Concentration of active ingredient in the spray mixture [ppm] | Degree of efficacy [% of the untreated control] |
|---|---|---|
| (A) | 4 | 0 |
| (B) | 4 | 0 |
| (D) | 16 | 39 |

TABLE B.2

Degree of efficacy of the mixture

| Mixture of active ingredients | Observed degree of efficacy | Expected degree of efficacy |
|---|---|---|
| 16 ppm (A) + 4 ppm (D); Mixing ratio 4:1 | 90 | 39 |
| 16 ppm (B) + 4 ppm (D); Mixing ratio 4:1 | 95 | 39 |

Test result: The observed degree of efficacy in all mixing ratios is higher than calculated in advance using Colby's formula.

We claim:

1. A fungicidal composition comprising a) a compound of the formula I

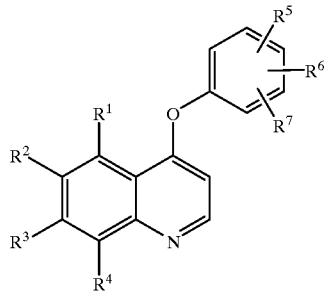

(I)

or an N-oxide or salt thereof, wherein $R^1$, $R^2$, $R^3$ and $R^4$ are hydrogen, hydroxyl, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$R^5$, $R^6$ and $R^7$ are hydrogen, hydroxyl, cyano, nitro, halogen, $C_1$–$C_7$-alkyl, $C_1$–$C_7$-haloalkyl, $C_1$–$C_7$-alkoxy, $C_1$–$C_7$-haloalkoxy, $C_1$–$C_7$-alkylthio, $C_1$–$C_7$-haloalkylthio, $C_1$–$C_7$-hydroxyalkyl, $C_2$–$C_4$-acyl, aryl or aryloxy, it being possible for the radicals with aryl to carry one to three of the following groups: cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, and d) (2RS,3SR)-1-[3-(2-chlorophenyl)-2-(4-fluorophenyl) oxiran-2-ylmethyl]-1H-1,2,4-triazole (IV)

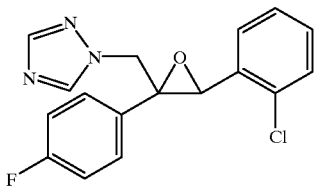

in a synergistically effective amount.

2. The composition defined in claim 1, wherein $R^1$, $R^2$, $R^3$ and $R^4$ are hydrogen or halogen, and $R^5$, $R^6$ and $R^7$ are hydrogen or halogen.

3. The composition defined in claim 1, wherein at least one of $R^1$ to $R^4$ is halogen.

4. The composition defined in claim 1, wherein $R^1$, $R^2$, $R^3$ and $R^4$ denote hydrogen, fluoro, chloro or bromo.

5. The composition defined in claim 1, wherein $R^5$ is halogen, $R^6$ is hydrogen or halogen and $R^7$ is hydrogen.

6. The composition defined in claim 1, wherein $R^5$, $R^6$ and $R^7$ denote hydrogen, fluoro, chloro or bromo.

7. The composition defined in claim 4, wherein at least one of $R^1$ to $R^4$ is fluoro, chloro or bromo.

8. The composition defined in claim 6, wherein $R^5$ is fluoro, chloro or bromo, $R^6$ is hydrogen, fluoro, chloro or bromo and $R^7$ is hydrogen.

9. The composition defined in claim 1, wherein the weight ratio of the compound I to the triazole (IV) is from 10:1 to 0.1:1.

10. A method of controlling fungal pests, which comprises treating the fungal pests, their environment or the plants, seeds, soils, surfaces, materials or rooms to be protected against said fungi with a synergistically effective amount of a compound of the formula I as defined in claim 1 and (2RS,3SR)-1-[3-(2-chlorophenyl)-2-(4-fluorophenyl)oxiran-2-ylmethyl]-1H-1,2,4-triazole (IV).

11. The method of claim 10, wherein $R^1$, $R^2$, $R^3$ and $R^4$ are hydrogen or halogen, and $R^5$, $R^6$ and $R^7$ are hydrogen or halogen.

12. The method defined in claim 10, wherein at least one of $R^1$ to $R^4$ is halogen.

13. The method of claim 10, wherein $R^1$, $R^2$, $R^3$ and $R^4$ denote hydrogen, fluoro, chloro or bromo.

14. The method of claim 10, wherein $R^5$ is halogen, $R^6$ is hydrogen or halogen and $R^7$ is hydrogen.

15. The method of claim 10, wherein $R^5$, $R^6$ and $R^7$ denote hydrogen, fluoro, chloro or bromo.

16. The method of claim 15, wherein at least one of $R^1$ to $R^4$ is fluoro, chloro or bromo.

17. The method of claim 13, wherein $R^5$ is fluoro, chloro or bromo, $R^6$ is hydrogen, fluoro, chloro or bromo and $R^7$ is hydrogen.

18. The method of claim 10, wherein the compound I and the triazole (IV) are applied jointly or separately, or in succession.

19. The method of claim 10, wherein from 0.01 to 0.5 kg/ha of the compound I are applied.

20. The method of claim 10, wherein from 0.1 to 1 kg/ha of the triazole (IV) are applied.

* * * * *

UNITED STATES PATENT AND TRADEMARK OFFICE
CERTIFICATE OF CORRECTION

PATENT NO. : 6,177,446 B1
DATED : January 23, 2001
INVENTOR(S) : Wagner et al.

Page 1 of 1

It is certified that error appears in the above-identified patent and that said Letters Patent is hereby corrected as shown below:

Column 16, claim 16,
Line 18, "claim 15" should be -- claim 13 --.

Column 16, claim 17,
Line 20, "claim 13" should be -- claim 15 --.

Signed and Sealed this

Twenty-third Day of October, 2001

Attest:

NICHOLAS P. GODICI
Attesting Officer  Acting Director of the United States Patent and Trademark Office